United States Patent [19]

Ash et al.

[11] Patent Number: 4,777,953
[45] Date of Patent: Oct. 18, 1988

[54] CAPILLARY FILTRATION AND COLLECTION METHOD FOR LONG-TERM MONITORING OF BLOOD CONSTITUENTS

[75] Inventors: Stephen R. Ash, Lafayette; Elsa M. Janle-Swain, West Lafayette, both of Ind.

[73] Assignee: Ash Medical Systems, Inc., West Lafayette, Ind.

[21] Appl. No.: 18,616

[22] Filed: Feb. 25, 1987

[51] Int. Cl.⁴ .............................................. A61B 5/05
[52] U.S. Cl. .................................................. 128/635
[58] Field of Search ............... 128/632, 635, 768, 769; 604/4, 29, 50, 66

[56] References Cited

U.S. PATENT DOCUMENTS

| | | | |
|---|---|---|---|
| 3,572,315 | 3/1971 | Cullen, II | 128/632 |
| 3,649,199 | 5/1972 | Littlejohn | 128/632 |
| 3,658,053 | 4/1972 | Fergusson et al. | 128/632 |
| 3,981,297 | 9/1976 | Dunn et al. | 128/632 |
| 3,983,864 | 10/1976 | Sielaff et al. | 128/632 |
| 4,187,856 | 2/1980 | Hall et al. | 128/635 |
| 4,221,567 | 9/1980 | Clark et al. | 128/635 |
| 4,265,249 | 5/1981 | Schindler et al. | 128/635 |
| 4,526,569 | 7/1985 | Bernardi | 604/4 |
| 4,633,878 | 1/1987 | Bombardieri | 128/635 |

OTHER PUBLICATIONS

Progress Toward a Potentially Implantable, Enzyme-Based Glucose Sensor, David A. Gough, John K. Leypoldt, and Jon C. Armour *Diabetes Care*, vol. 5, No. 3, May–Jun. 1982.
Enzymatic Glucose Electrodes, George G. Guilbault—*Diabetes Care*, vol. 5, No. 3, May–Jun. 1982.
Implanted Electroenzymatic Glucose Sensors, Leland C. Clark, Jr. and Carol A. Duggan—*Diabetes Care*, vol. 5, No. 3, May–Jun. 1982.
Use of Wearable Artificial Pancreas to Control Diabetes, M. Shichiri, R. Kawamori, Y. Goriya, Y. Yamasaki, N. Hakui, N. Asakawa, H. Abe, First Department of Medicine, Osaka University Medical School, Osaka, Japan.
A Miniature Glucose Sensor Implantable in the Blood Stream, T. Kondo, K. Ito, K. Ohkura, K. Ito, S. Ikeda—*Diabetes Care*, vol. 5, No. 3, May–Jun. 1982.
Comparison of O₂ Electrode Type and H₂O₂ Electrode Type as a Glucose Sensor for the Artificial B-Cell, S. Ikeda, K. Mino, K. Ito, K. Ichikawa, H. Ichihashi, T. Kondo, Nagoya University School of Medicine, Nagoya, Japan.
Measurement of Glucose Concentration in the Presence of Coreactants with a Platinum Electrode, H. Lerner, J. S. Soeldner, C. K. Colton, Jose Giner—*Diabetes Care*, vol. 5, No. 3, May–Jun. 1982.
Amperometric Glucose Sensor: Short-Term In Vivo Test, Jan J. Lewandowski, Ewa Szczepanska-Sadowska, Janusz Krzymien, Maciej Nalecz—*Diabetes Care*, vol. 5, No. 3, May–Jun. 1982.
Affinity Sensor: A New Technique for Developing Implantable Sensors for Glucose and Other Metabolites, Jerome S. Schultz, Sohrab Mansouri, Irwin J. Goldstein—*Diabetes Care*, vol. 5, No. 3, May–Jun. 1982.
Noninvasive Glucose Monitoring of the Aqueous Humor of the Eye: Part I. Measurement of Very Small Optical Rotations, B. Rabinovitch, W. F. March, Robert L. Adams—*Diabetes Care*, vol. 5, No. 3, May–Jun. 1982.

(List continued on next page.)

*Primary Examiner*—Max Hindenburg
*Attorney, Agent, or Firm*—Woodard, Emhardt, Naughton Moriarty & McNett

[57] ABSTRACT

A method and device for long term monitoring of the blood level of various blood constituents. The monitoring is accomplished by capillary filtration and collection of an ultrafiltrate of blood. Filtration of the ultrafiltrate occurs through a filter composed of hollow fibers which are implanted within an interstitial body space in fluid communication with blood capillaries. The ultrafiltrate is drawn through the filter and into an ultrafiltrate collector which extends externally of the body. The collector provides a vacuum for withdrawing the ultrafiltrate and holds discrete liquid samples of the ultrafiltrate. The method and device is particularly suited for long term monitoring of blood glucose levels in diabetic patients or other blood chemical constituents in other patients.

5 Claims, 4 Drawing Sheets

OTHER PUBLICATIONS

Noninvasive Glucose Monitoring of the Aqueous Humor of the Eye: Part II. Animal Studies and the Scleral Lens, W. F. March, B. Rabinovitch, R. L. Adams—*Diabetes Care*, vol. 5, No. 3, May–Jun. 1982.
A Hollow Fiber Osmotic Glucose Sensor, E. Janle-Swain, M. Szentes, S. R. Ash—*New Forms of Therapy*, 176 A, No. 671.
Telemetry Glucose Monitoring Device with Needle-Type Glucose Sensor: A Useful Tool for Blood Glucose Monitoring in Diabetic Individuals, M. Shichiri, N. Asakawa, Y. Yamasaki, R. Kawamori, H. Abe, *Diabetes Care*, vol. 5, No. 3, May–Jun. 1982.

CAPILLARY FILTRATION AND COLLECTION METHOD FOR LONG-TERM MONITORING OF BLOOD CONSTITUENTS

BACKGROUND OF THE INVENTION

The subject invention relates generally to the field of medical devices and methods for monitoring physiological parameters of the body and, more particularly, such devices and methods which are capable of monitoring on a long-term basis various physiological constituents present in the bloodstream.

Six million Americans have diabetes mellitus. On some schedule, all of these patients need to monitor their blood glucose levels to keep their disease under control. This monitoring is done by urine testing, which indirectly reflects blood glucose, by intermittent blood glucose tests by venipuncture or blood glucose monitoring by finger prick and strip analysis. There are many inaccuracies associated with urine testing, and many patients are reluctant to do an adequate number of blood tests because of the pain involved. As a result many diabetics do not maintain good glucose control.

Growing evidence proves that poor glucose control is a causative factor in development of the secondary complications of diabetes. These secondary complications take a great toll in morbidity and mortality. Twenty to twenty five per cent of End Stage Renal Disease is caused by diabetes. About 5000 diabetics become blind annually, and about 20,000 require amputations. Diabetes increases the risk of cardiovascular disease and diabetics also suffer from painful and sometimes disabling neuropathies.

The monetary cost for the treatment of the secondary complications of diabetes is extremely high. The current cost of dialysis for End Stage Renal Disease is about $25,000 per patient annually. The annual hospital costs for amputations is presently about $250 million. Disability payment and rehabilitation services for blind diabetics cost about $45 million annually.

The best prospect for reducing the morbidity and mortality of diabetes lies in technological developments which will provide better blood glucose control. Insulin infusion pumps and finger-stick home blood glucose monitoring are steps in that direction. The development of an implantable glucose monitoring device would make home blood glucose monitoring simpler, less painful and more acceptable for the diabetic population. This would be a significant step toward improving blood glucose control since it would provide much more information than available with any current method of glucose monitoring. The greatly increased knowledge of blood glucose levels obtained by an implantable monitoring system would permit analysis of the basic kinetic parameters of insulin in each patient, e.g. insulin sensitivity and half life. Also, a reliable long term glucose sensor could be combined with automatic insulin infusion systems already available to form an "artificial pancreas". With such a device it would be possible to maintain blood glucose within normal limits with little patient intervention.

The only hospital use instrument which has been on the market for constant blood glucose monitoring is the Biostator, manufactured by Miles Laboratories, Inc., Elkhart, Ind. This instrument constantly withdraws blood to monitor blood glucose concentration and infuses insulin in response to the blood glucose level. This type of instrument is very expensive and is therefore available in only a relatively few hospitals. Further, because the Biostator device requires a continuous flow of blood without return to the patient there is a limit on the amount of time over which the instrument can be used, and there are also problems and risks involved with the vascular access.

A number of different approaches have been taken to develop an implantable glucose sensor. Most approaches utilize a chemical reaction of glucose which actually consumes the glucose in the process of measuring it. Thus they are sensitive to the mass transfer coefficient of glucose to the sensor. Fibrous tissue formation around the sensor changes the calibration of the device. Secondly, those with enzyme components suffer degradation of the enzyme after several days of use.

Enzymatic glucose electrodes utilize an immobilized enzyme, glucose oxidase, which reacts selectively with glucose, in conjunction with an ion selective electrode which measures the decrease of one of the reactants ($O_2$) as reported in Gough D.A. et al.: Progress toward a potentially implantable, enzyme-based glucose sensor. *Diabetes Care* 5:190–198, 1982, or the increase of one of the products ($H_2O_2$). The change in potential or current at the electrode can be used to make kinetic measurements or the steady state current or potential can be used for equilibrium measurements as disclosed in Guilbault G.G.: Enzymatic glucose electrodes. *Diabetes Care* 5:181–183, 1982.

An electroenzymatic sensor disclosed in Clark et.al.: Implanted electroenzymatic glucose sensors. *Diabetes Care* 5:174–180, 1982 involves the enzymatic oxidation of glucose by glucose oxidase and the production of $H_2O_2$. The $H_2O_2$ is measured voltametrically at a Platinum electrode. The current produced by $H_2O_2$ is directly proportional to the glucose in blood, plasma or tissue fluid in the 0 to 100 mg/dl region. At higher glucose concentrations there is a non-linear increase in current with increasing glucose concentration.

A glucose oxidase electrochemical sensor which detects the production of $H_2O_2$ has been made in a needle form and has functioned up to 3 days in subcutaneous tissue as reported in the publication Shichiri M. et al.: Use of wearable artificial pancreas to control diabetes. *Progress in Artificial Organs* 782–787, 1983. When this sensor was coupled with a micro-computer and an insulin infusion system, glucose control was achieved which was superior to that achieved with conventional treatment. After three days there was a fixation of proteins and blood cells to the membrane of the electrode, resulting in diminished function.

An $O_2$ sensitive enzymatic glucose sensor which can be inserted into an arterio-venous shunt is disclosed in the following publication: Kondo T. et al.: A miniature glucose sensor, implantable in the blood stream. *Diabetes Care* 5:218–221, 1982. This sensor can function 200 hours with a 10% loss in activity. Another publication, Ikeda et al.: Comparison of $O_2$ electrode type and $H_2O_2$ electrode type as a glucose sensor for the artificial B-cell. *Prog. in Artificial Organs* 773–777, 1983 compared the in vivo function of the $O_2$ sensor with a $H_2O_2$ electrode in a vascular access and found the $O_2$ electrode responded better to changes in blood glucose. However, this sensor is impractical because of the amount of vascular surgery necessary to install the shunt.

Another approach to a glucose sensor is the catalytic electrode sensor, which is based on the electrochemical oxidation of glucose on a platinum electrode. Such sensors are reported in the following publications: Lerner H. et al.: Measurement of glucose concentration with a platinum electrode. *Diabetes Care* 5:229-237, 1982; Lewandowski J.J. et al.: Amperometric glucose sensor: Short-term in vivo test. *Diabetes Care* 5:238-244, 1982. The applied voltage is varied and the current response is measured. The current-voltage curves vary with glucose concentration. Other substances, such as amino acids and urea, can affect the output of this sensor, but use of a compensated net charge method of evaluating the response improves the sensitivity. Another problem is change in the loss in catalytic activity over time. Overall, this type of sensor has not demonstrated the selectivity or sensitivity necessary for a useful glucose sensor.

Several other technologies for glucose sensors depend on chemical or physical properties of glucose such as its affinity for lectins described in Schultz J.S. et al.: Affinity sensor: A new technique for developing implantable sensors for glucose and other metabolites, *Diabetes Care* 5:245-253, 1982, its optical rotation in solution described in Rabinovitch B. et al.: Non-invasive glucose monitoring of the aqueous humor of the eye: Part I. Measurement of very small optical rotations, *Diabetes Care* 5:254-258, 1982; and March W. F., et al.: Non-invasive glucose monitoring of the aqueous humor of the eye: Part II. Animal studies and the scleral lens, *Diabetes Care* 5:259-265, 1982, or its osmotic effect, Janle-Swain E. et al.: A hollow fiber osmotic glucose sensor, *Diabetes* 33: Supp. 1, 176A, 1984. These approaches do not consume glucose, but rather depend on the concentration of glucose at the device site reaching an equilibrium with tissue glucose. None of these devices have proven to be totally satisfactory.

In the Schultz et al. study, a monitoring system is disclosed which operates based on the ability of glucose and a fluorescein-labeled dextran to bind competitively to the lectin Concanavalin A (Con A). Con A can be bound to the inside of a hollow fiber through which glucose can diffuse. Fluorescein labeled dextran is added to the inside of the fiber. The amount of fluorescein labeled dextran is added to the inside of the fiber. The amount of fluorescein-labeled dextran displaced from the Con A is measured by an argon laser fiber optic system. This system has responded to differences in glucose concentration in vitro, but less than the theoretical response was obtained. In vitro tests have demonstrated that the Con A can remain bound to the fibers for eight days.

Another study, Shichiri M. et. al.: Telemetry glucose monitoring device with needle type glucose sensor: A useful tool for blood monitoring in diabetic individuals, *Diabetes Care* 9:298-301, 1986, supports that measurement of glucose in the subcutaneous tissue does provide an adequate indication of blood glucose. This study discloses a correlation in diabetic patients between tissue glucose and blood glucose, with correlation coefficients ranging from 0.89 to 0.95. This work indicates a five minute delay between changes in blood glucose and subcutaneous tissue glucose, with tissue glucose being 6 to 22% lower than blood glucose. This decrease in subcutaneous glucose versus blood glucose is due to the metabolism of glucose by subcutaneous tissue. The level of glucose which is obtained depends upon the metabolic rate of the subcutaneous tissue, the blood flow, the degree of fibrous tissue in the space, and the rate of fluid transfer across the capillary wall.

The goal of all of these studies was to develop sensors for permanent subcutaneous placement. Currently there does not exist an implantable glucose sensor which will function for an extended period of time in vivo. There are a number of sensors which function in vitro and some which function well for a few days in vivo, but none have proved effective over long periods of time. Measurement of blood glucose is done by diabetic patients at home by the finger-stick method. A drop of blood is placed on a paper strip impregnated with glucose oxidase and a chromophore. The color change produced by the glucose in the blood is determined visually or with a small hand held reflectance meter. In hospitals blood glucose may be measured at the bedside by the same finger-stick and strip method used by patients at home or venous blood samples may be analyzed automatically in the laboratory using glucose analyzers which are usually based on spectrophotometric or electrocatalytic analysis methods.

SUMMARY OF THE INVENTION

A capillary filtration and collection system for long term sampling of an ultrafiltrate of blood according to one embodiment of the present invention comprises a porous filter made of a material compatible for long-term patency inside the body in fluid communication with blood capillaries and having pore sizes not greater than approximately 300,000 daltons. There is further provided an ultrafiltrate collector connected to the filter in fluid communication therewith and adapted to extend externally of the body with the filter implanted inside the body. A vacuum generating means is also provided for withdrawing the ultrafiltrate through the filter and into the ultrafiltrate collector.

The present invention also comprises a method for continuously monitoring the blood level of a physiological constituent of blood. According to one embodiment of the method, a porous fiber filter is implanted within the body in fluid communication with blood capillaries. One desirable location for placement of the filter is in the subcutaneous tissue, where it removes fluid through capillary walls and through the gelatinous subcutaneous tissues. Other possible locations include within the muscles of the bowel wall or peritoneum. An ultrafiltrate of blood is filtered from the capillaries by exerting a negative pressure within the porous fiber filter so as to cause the ultrafiltrate to flow by convection from the capillaries through the filter at a desired flow rate. The ultrafiltrate is then collected in a reservoir located externally of the body from which it is periodically removed to allow chemical measurement of a physiological constituent, such as glucose, present in the ultrafiltrate. Alternatively, fluid is removed and immediately transferred to a measurement device.

ADVANTAGES

The device and technique of the present invention offers a unique approach to the problem of continuous blood glucose measurement. Other attempts at the development of an implantable glucose monitor have sought to make the entire system implantable. Making the fluid removal portion internal and the measurement system external eliminates many of the problems that arise from a totally implantable system and increases the options for glucose measurement. Among these options are optical paper strip methods for the measurement of glucose. Such methods, which have been well developed, require consumable supplies and are well suited for use in an external system. There are also other options for external measurement systems, such as the use of catalytic enzyme electrodes. These have a limited in vivo lifetime which limit their usefulness in an implantable sensor, but they can be easily replaced if used externally. Thus, when used with the present invention, they could serve as a workable alternative to paper strips for glucose measurement outside the body.

The implantable fiber system of the present invention has great potential for use by diabetics in self-monitoring of glucose levels in their own home. Patients may monitor their glucose levels at home using commercially available strips and reflectance meters as often as six times an hour without the necessity of sticking themselves and drawing blood. Alternatively, the patient may wear the sample collector which will collect samples over a 3-5 hour period. Fluid samples in the collector can be analyzed at a convenient time either by the patient or at the doctor's office. The collector may be used with an optical monitoring system which we are developing which will automatically withdraw and analyze samples and mathematically relate the sample to the collection time. Manual analysis of samples from the collector would also be possible by conventional methods. The painlessness of such a monitoring system offers the possibility of better control for diabetics because it is more likely to be faithfully used.

The subject invention could also be used in a hospital environment. An intensive care unit version of the invention would perform glucose measurements in a continuous manner using the same type of implantable filter used in out-patient applications. Because only small amounts of ultrafiltrate are needed for analysis of glucose levels using the present invention and because the device is not within the blood vessels and because red blood cells are not lost, the only limit on the length of time that the device of the present invention could be used would be the useful life of the filter unit in the body. Since the filtrate is a clear liquid rather than blood, chemical analysis is easier. An automatic hospital glucose monitor developed for use with the subject invention would be less complex and therefore less expensive than vascular access/continuous blood withdrawal glucose monitoring systems such as the Biostator device, thus making such a system financially feasible for more hospitals. This machine can be identical to the one used for intermittent analysis of samples from the above mentioned collecting reservoir.

The subject invention would provide improved control of blood glucose over the current hospital practice of venipuncture or finger-stick glucose monitoring in diabetics. Glucose monitoring could be performed at virtually any desired interval. The discomfort of repeated venipunctures or finger sticks would be eliminated along with the necessity of having lab personnel periodically visiting the patient to draw blood. In addition, there would be none of the delays involved in obtaining glucose concentration results from the laboratory. Treatment decisions could be made much more rapidly and the time needed to obtain good glucose control would be shortened. Improved control, in most cases, will hasten recovery and shorten hospital stays. Effective storage and display capability of the data would also mean that the information would be readily available whenever needed.

In addition to monitoring glucose, the subject invention may also be useful in monitoring and measuring the levels of other physiological or pharmacological substances present in blood. Some preliminary testing has indicated that sodium and potassium could be monitored using the capillary filtration and collection techniques of the present invention. Measurement of BUN, drug or hormone levels and capillary blood gases ($CO_2$ and $O_2$) are other potential applications of a capillary filtrate collector. Such systems would be highly cost effective and would also provide nearly constant clinical monitoring without the need for intermittent drawing of venous blood samples. The subject device may be of particular use in neonates or pediatric patients where drawing blood is a difficult and trying experience.

Accordingly, it is an object of the present invention to provide an improved method and device for monitoring the blood level of a physiological constituent of blood.

Related objects and advantages of the subject invention will become more apparent by reference to the following drawings and detailed description.

DESCRIPTION OF THE PREFERRED EMBODIMENT

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The approach of the subject invention to the problem of constant long term glucose monitoring is to apply a negative pressure to ultrafiltration fibers implanted in interstitial spaces, such as subcutaneous tissue, and withdraw a plasma ultrafiltration from blood capillaries located in the region around the fibers. The fibers remove the plasma ultrafiltrate by convection. The fluid quickly leaves the blood capillaries, transverses the interstitial space between the capillaries and the fiber filter and enters the filter.

In convective transfer of fluid across membranes, chemicals smaller than the pore size of the membranes remain at the same concentration on either side of the membrane. The pore size of a blood capillary is approximately 50,000 daltons. Therefore, if a fiber is used with a pore size of 30,000 daltons, then low molecular weight non-protein bound chemicals such as glucose, sodium, potassium, urea, creatinine, $O_2$ $CO_2$ etc. will appear in the ultrafiltrate at the same concentration as in the blood. The rate of transfer of the fluid through the interstitial tissues is sufficiently fast that metabolism of chemicals by interstitial tissue cells will not cause a significant decrease in concentration of glucose or other chemicals. Present studies indicate that fluid flow rates between about 20 to 500 microliters per hour are acceptable for this purpose.

Figure 1:
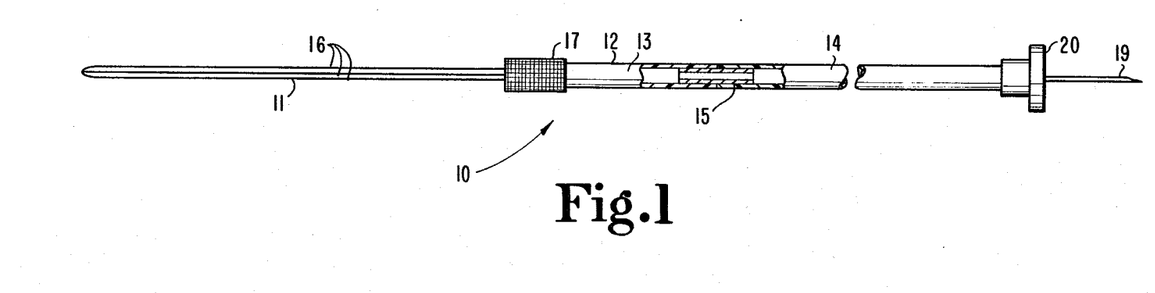
FIG. 1 is a fragmentary elevational view, partially in section, showing the capillary filtration device of the present invention.
Figure 1A:
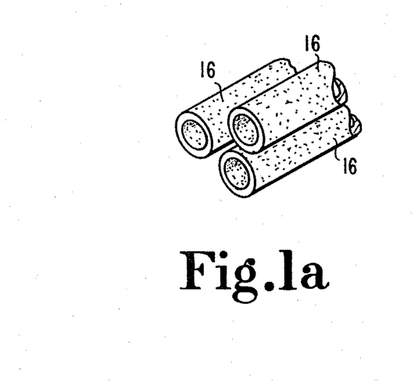
FIG. 1a is an enlarged fragmentary perspective view showing a section of the fibers depicted in FIG. 1.

A first embodiment of the capillary filtration device 10 of the present invention is illustrated in FIGS. 1 and 1a. Generally, the device 10 includes a filter 11 comprised of one or more implantable filter fibers 16 connected to a length of conducting tubing 12 which serves as a means to collect ultrafiltrate fluid passing through filter 11 externally of the body. The conducting tubing 12 is comprised of a short section 13 of silicone or polyurethane tubing adapted to extend inside the body and a longer section 14 of polyvinylchloride (PVC) tubing adapted to extend externally of the body. A rigid metal tube 15 of relatively short length extends inside silicone tubing section 13 and PVC tubing section 14 at their juncture and serves to permit the silicone and PVC tubing sections to be heat sealed together without allowing the lumen to collapse.

As seen clearly in FIG. 1a, in one configuration the filter 11 is formed of three elongate ultrafiltration fibers 16 having a hollow tubular shape. An alternative embodiment of the invention shown in FIG. 1b incorporates a filter configuration 11' formed of two elongate ultrafiltration fibers 16 having both their ends secured by adhesive inside the lumen of tubing section 13 so as to form a loop. This alternative configuration makes the implanted portion of the device shorter and therefore increases patient acceptability. The loop configuration also holds the fibers apart slightly and therefore increases the surface area exposed to tissue. The fibers 16 are fixed at their proximal ends by an adhesive inside the lumen of the tubing section 13.

In the FIG. 1a elongated filter configuration, the distal ends of the fibers 16 are secured together by heat sealing while the proximal ends are secured to the lumen wall of tubing section 13 by an epoxy or polyurethane adhesive. A cuff 17 is secured around the silicone tubing section 13 at the junction of the fibers 16 and tubing section 13. The purpose of cuff 17 is to allow tissue ingrowth into the cuff and seal off any path for passage of skin bacteria around the device, and also to serve as an anchoring means to anchor the device in the body after sutures are removed. Cuff 17 is preferably made of material which promotes ingrowth of fibroblast and fibrous tissue. Suitable materials are Dacron, PTFE or textured polyurethane.

The purpose for the silicone (or polyurethane) and PVC tubing sections is that it has been found that silicone tubing bonds better to the cuff 17 and fibers 16 than PVC tubing and has improved the biocompatibility of the device in the body. The PVC tubing is preferred for the remainder of the length of conducting tubing because it is sufficiently rigid so that it will not collapse under negative pressure conditions during operation while also possessing good flexibility and a low permeability to air when placed under vacuum. It also serves as a pumping segment for a roller pump which is one method of creating a vacuum for fluid removal.

At the proximal end of the tubing section 14 there is an 18 gauge hollow needle 19 and hub 20 which serves to facilitate the transfer of the ultrafiltrate fluid from the conducting tubing into a suitable reservoir or a chemical analysis machine.

Figure 8:
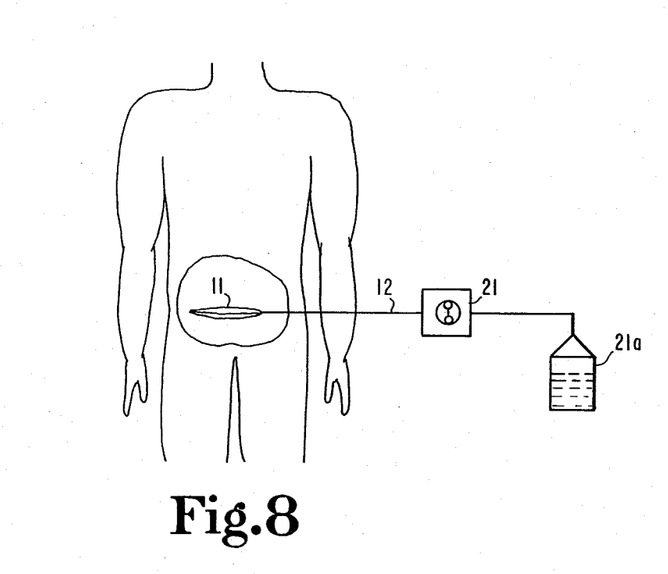
FIG. 8 is a diagrammatic view of the capillary filtration device with the filter portion inside a body and the device equipped with a roller pump.

Negative pressure for ultrafiltrate fluid removal can be accomplished by evacuating air from the conducting tubing 12 with a syringe (FIG. 2) or a pre-evacuated rigid container such as a "vacutainer" tube. Alternatively, the fluid may be removed by inserting a segment of the tubing section 14 into a roller pump 21 depicted in FIG. 8 which pumps the fluid into a reservoir 21a or into a chemical analysis machine. A suitable roller pump for this purpose is a perisaltic roller pump manufactured by Cormed, Inc. of Medina, N.Y. This pump generates a vacuum of over 700 mmHg. For the ambulatory hospital patient or for home use, however, a withdrawal system based on vacuum alone is preferred because the need for pumps and an associated power supply, such as electrical batteries, is eliminated.

At high negative pressures (−300 to −750 mmHg) the device removes approximately 10 volumes of gas per volume of liquid from the subcutaneous space. It has been found in animal tests of this device that if the lumen of the conducting tubing 12 is sufficiently small in diameter, the ultrafiltrate fluid passing through the tubing will remain in distinct boluses separated by air. Tubing having an inner diameter less than about 0.115" should be practicable for this purpose, while an inner diameter of 0.045–0.055" is more preferred. This phenomena is useful in conducting time studies of the fluid samples based on their position along the length of the tubing. In addition, the gas speeds transfer of the liquid samples through the conducting tubing.

Figure 2:
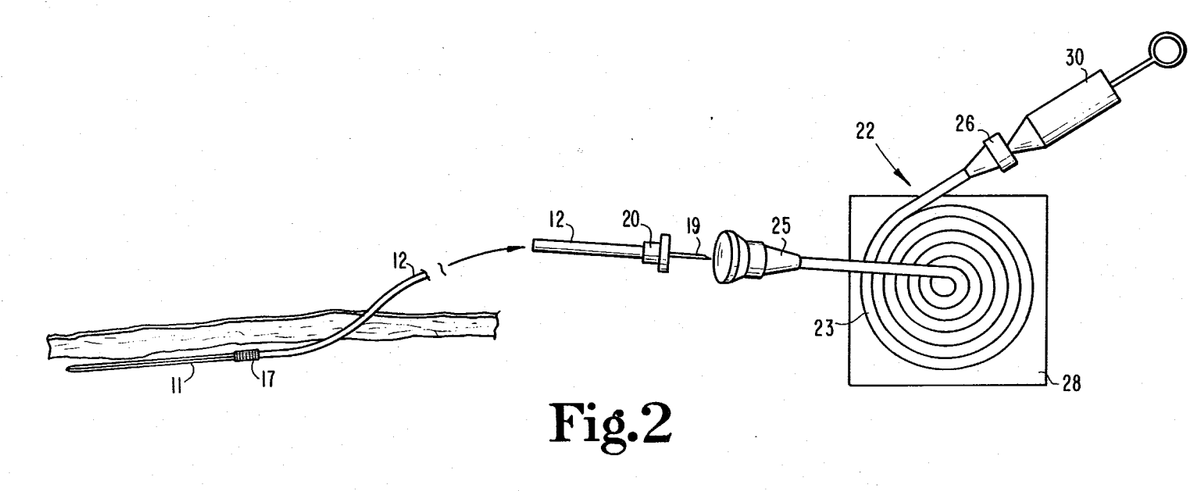
FIG. 2 is a diagrammatic view of the capillary filtration device with the filter portion inside a body and the device equipped with a coiled tube collector and a syringe evacuating the collector.

A fluid collection device is shown in FIG. 2 which provides vacuum for filtrate removal and preserves the separation of fluid samples which occurs in the conducting tubing 12. A mathematical analysis can later determine the relationship between time and sample position at the end of the use of the collector. As illustrated in FIG. 2, the collector 22 includes a coil of flexible plastic tubing 23 having a needle hub 25 for receiving needle 19 at one end, and an injection/sampling port 26 at the other end. The hub 25 and port 26 are of conventionally known construction. The tubing 23 is coiled on a layer of transparent adhesive tape 28 and is covered on the opposing side with another layer of tape. The tape stabilizes the tubing and also decreases air permeation into the tubing. With the collector attached to the conducting tubing 12 by insertion of needle 19 into hub 25, the collector can be evacuated with a syringe 30 through port 26 to provide the negative pressure for fluid withdrawal. When the collector 22 is filled the collector may be removed and replaced with a new collector. The ultrafiltration samples may be removed from the collector for sampling through injection port 26.

The relationship between the sample position along the length of coiled tube 23 and time depends on the method of vacuum application. If a roller pump is used on tubing section 14 with port 26 open, the negative pressure is uniform over time. This results in a linear relationship between sample position and time. If the sole source of vacuum pressure is from evacuating air from the coiled tubing, then the vacuum pressure will decrease with time. The small fluid samples will be collected more rapidly when the collector is first attached and evacuated and more slowly as the vacuum decreases logarithmically over time. However, the relationship between time and sample position can still be determined mathematically.

Two different types of ultrafiltration fibers have been tested in laboratory animals. The first type are AN-69 polyacrylonitrile (PAN) fibers used in the Hospal Filtral dialyzer manufactured by Rhone Poulenc Industries of Paris, France. These fibers have homogeneous walls with 30,000 dalton molecular weight cut off and a filtration rate of 20 ml./hr.*m.$^2$*mmHg. The second type of fibers which have been tested are P-100 polysulfone fibers manufactured by Amicon Corporation of Danvers, Mass. The Amicon polysulfone fibers come in a variety of dimensions with a variety of molecular weight cut offs. These fibers have a porous thin 1-2 micron skin on the luminal side of the fiber and a porous rough outer surface. Due to breakage problems with the Amicon polysulfone fibers after implantation, the PAN fibers are presently preferred. However, stronger polysulfone fibers than the Amicon polysulfone fibers which have previously been used and fibers with a smooth outer skin are manufactured by A/G Technology Corporation of Needham, MA. It is perceived that other types of polymer hollow fibers could also be suitably employed, such as for example either polypropylene or polycarbonate fibers.

Preferably the molecular weight cut off of the pore size of the fiber needs to be less than approximately 300,000 daltons to exclude fibrinogen protein molecules from the ultrafiltrate which would otherwise promote clot formation within the conducting tubing. If an optical monitoring system is used to measure glucose, the molecular weight cutoff should be less than about 60,000 daltons to exclude hemoglobin from the ultrafiltrate. Because the molecular weight of glucose is approximately 180, the molecular weight cutoff of the fiber could be as small as 1000-2000 daltons without affecting the transmission of glucose through the fiber. However, with molecular weight cutoffs of 30,000-50,000 daltons other molecules such as uric acid, vitamin $B_{12}$, insulin, etc. could be measured in the filtrate. A molecular weight cutoff in the range of 30,000 to 50,000 daltons is suitable for these reasons.

It is well known in the field of blood filtration that if proteins are excluded by a membrane, layers of protein will form on the blood side of the membrane and diminish the flow of fluid. Stability of fluid removal rate from the current device has been demonstrated for 3-39 days of implantation. In the body interstitial spaces the lymphatic system serves to remove excess protein from around the fibers to maintain constant flow of filtrate.

The number, size and length of the fibers may also be varied within certain design considerations. For example, in the case of the polysulfone fibers, because of their thickness only one fiber has been used. When much thinner fibers are used, such as the PAN fibers, it is possible to increase the number of fibers which are employed to increase the ultrafiltrate flow rate and still permit the fibers to be subcutaneously implanted through a hollow needle. Polysulfone fibers have been used having lengths of about 20-25 cm. For the PAN fibers, a length of 17 cm. has been found to provide acceptable flow rates.

Figure 9:
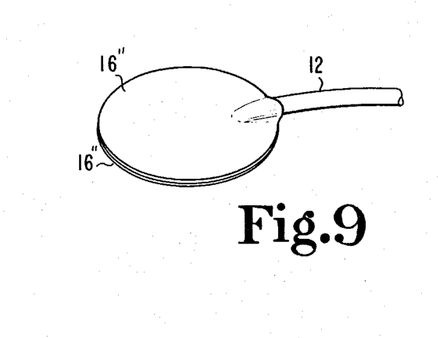
FIG. 9 is a fragmentary perspective view showing an embodiment of the filter of the present invention having two flat sheet membranes.

It may also be possible to change the configuration of the filter from hollow fibers to other configurations, such as flat sheet polymeric membranes 16, shown in FIG. 9, glued or otherwise fixed together around their circumferences to form two-sided membrane filters.

The flow rate of ultrafiltrate depends upon a number of factors, including the size and configuration of the filter and the amount of vacuum applied. The ultrafiltrate sample size necessary for the particular assay procedure determines the desired flow rate and vacuum. To some extent, these factors will in turn be dependent upon whether the device is being used at home for periodic glucose monitoring or for continuous monitoring in hospital applications. Since most glucose analysis methods require a sample size of at least five microliters and since continuous glucose monitoring for hospital patients coupled with automatic insulin infusion would require sampling at least as frequent as every 15 minutes, it is perceived that a minimum flow rate of 20 microliters per hour is desirable.

Figure 3:
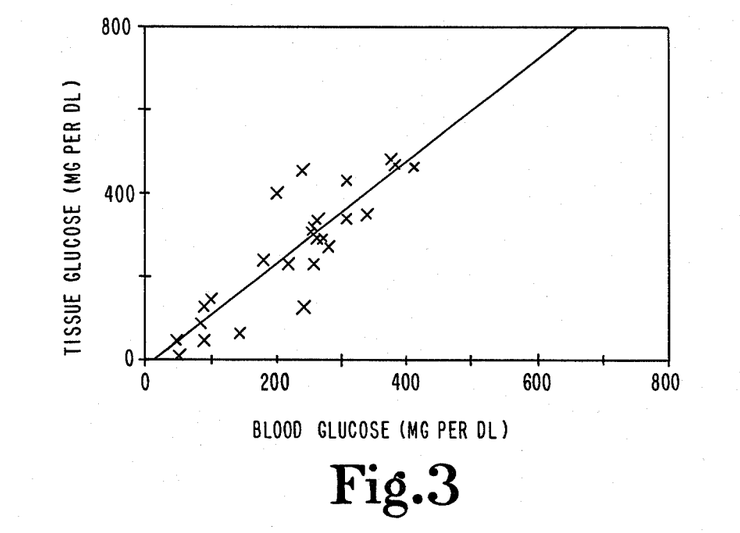
FIGS. 3 and 4 are graphs illustrating the relationship between blood glucose and tissue glucose found in test animals using the present invention.
Figure 4:
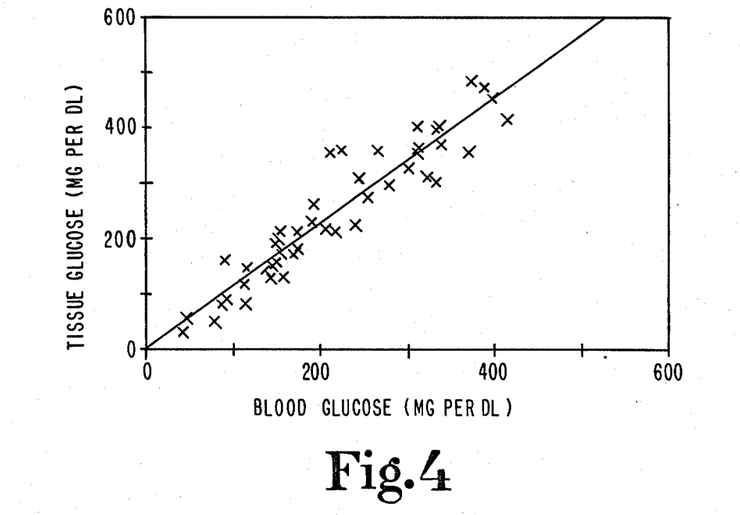

The present invention has been successfully tested in vivo in diabetic dogs for periods as long as 39 days. Glucose levels in the ultrafiltrate were compared to venous blood glucose levels and were very highly correlated. FIGS. 3 and 4 are graphs illustrating the correlation between blood glucose and filtrate glucose levels observed in two test dogs using the device of the present invention. In both of the tests, PAN fibers were used as the filtering medium. Filtrate fluid samples were collected over half hour intervals. Blood samples were collected either at the end of the filtrate sample collection period or at the mid-point of the collection period. Glucose was analyzed using blood glucose test strips and a reflectance meter. Regression analysis of the blood an ultrafiltrate glucose yielded correlation coefficients of $r=0.840-0.878$, $p=0.000$.

Figure 5:
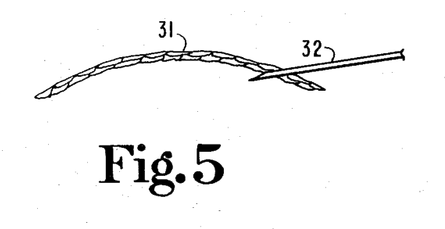
FIGS. 5-7 depict successive stages in performing the method of the implantation.
Figure 6:
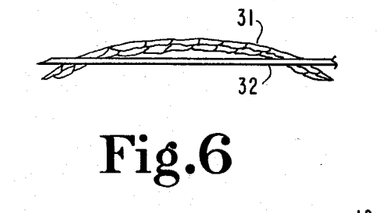

One method for placement of the device of the present invention for long term monitoring of blood glucose in a patient is performed as follows. Two small scalpel incisions spaced apart approximately the length of the fibers are made into the skin 31 of a locally anaesthesized patient at a suitable subcutaneous location, such as on the leg, buttocks, abdomen or arm of the patient. A hollow introducer needle 32 is advanced into the skin through the proximal incision (FIG. 5) and tunneled through the subcutaneous tissue space until the distal needle end is caused to exit the skin through the distal incision (FIG. 6). The fiber filter 11 portion of the device 10 is then inserted inside the hollow needle 32 until the cuff 17 stops at the proximal end of the needle. As the needle is pulled out, the distal end of the cuff is positioned beneath the skin.

Figure 7:
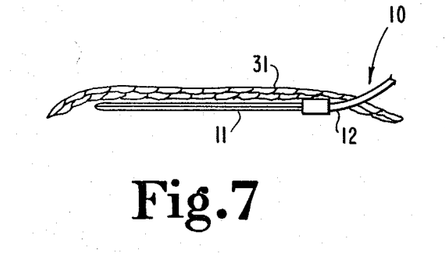

If the fibers are too flimsy, it may not be possible to directly thread them into the hollow needle 32. However, a nylon loop can be tied to the distal end of the fibers and a suture thread attached to the loop to aid in advancing the fibers into the hollow needle. While holding the device 10 in place, the needle is then pulled out of the skin from the distal incision, leaving the fibers, cuff and distal portion of the conducting tubing implanted in the subcutaneous tissue space (FIG. 7). Once the fibers are implanted, the suture and loop can be cut off and removed. A skin suture helps to close the incision over the cuff in a similar manner as for Tenckhoff peritoneal catheters. This suture is removed after the position of the cuff is stabilized by fibrous tissue ingrowth into the cuff.

Figure 1B:
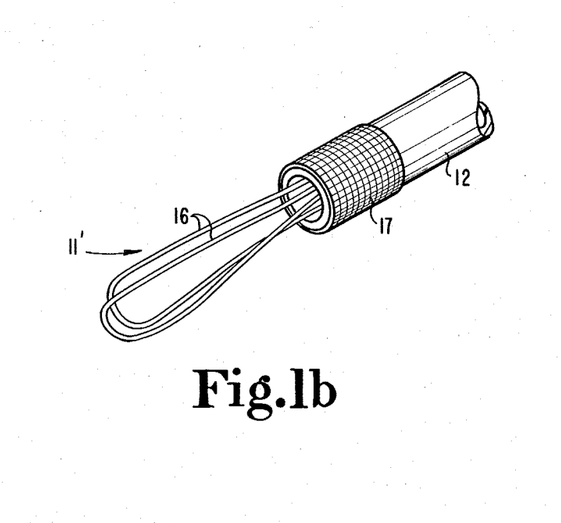
FIG. 1b is an enlarged fragmentary perspective view showing an embodiment of the filter of the present invention having two fibers in a loop configuration.

An alternative placement method is possible with the FIG. 1b embodiment of the invention having looped PAN fibers and a cuff sized to permit insertion of the device inside the lumen of an 11 gauge, 8 cm long hollow needle. With this embodiment, the needle is advanced subcutaneously through a single small incision. After full penetration of the subcutaneous tissues, the needle is withdrawn while the device is left in position.

After implantation according to either of the above described methods, a vacuum withdrawal force is applied to the conducting tubing, either by use of a roller pump or evacuating the air inside the sample collector with a syringe (FIG. 2). Fluid will then begin to flow from blood capillaries in the region around the fibers by convection and filter into the fibers. The ultrafiltrate fluid flows through the hollow space inside the fibers and into the conducting tubing for collection externally of the body in collector 22. Sampling of the ultrafiltrate in order to measure glucose level may be accomplished by virtually any conventionally known method for measuring glucose concentration in a fluid. When a relatively low frequency of sampling is desired, such as in home use applications, standard solid phase chemistry test strip methods for glucose may be used. In this measurement method, the ultrafiltrate is placed on a paper test strip containing glucose oxidase and a chromophore. The rate of color change of the test strip is a function of the glucose concentration and is measured by transmission spectrophotometry with a reflectance meter. In hospital situations, more sophisticated sampling means may be available, such as automatic glucose analyzers using spectrophotometric or electrocatalytic analysis techniques, and therefore can be employed.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected. For example, it is perceived that the present invention may prove useful in providing a whole series of monitors for physiological variables in either home or hospital use. Hospital monitors could be developed for multiple variable monitoring. In these monitors individual modules containing the solid phase chemistry could be made for each variable. The doctor would determine which variables were to be measured and the appropriate modules could be plugged into the fluid withdrawal system.

In order to avoid the possibility of air flowing back into the tubing and allowing the entry of air borne bacteria into the tubing, it is perceived that a bacteriological filter may be employed with the device so that only filtered air can enter the system.

To provide automatic continual analysis of blood glucose in the filtrate, a machine could be developed to measure glucose concentration in the filtered fluid. Such a machine would be useful in both home and hospital settings. In such a machine, a roller pump could be used to continually extract the fluid from the fiber or the collection reservoir. For critically ill patients the capillary ultrafiltrate could flow directly into the assay machine for real time glucose monitoring. For the hospitalized patient who is not confined to bed, the fluid may be collected in the reservoir and analyzed at desired intervals to provide a recent history of glucose levels. This information could be electronically transferred to a computer program for data processing. For home use, the patient could have the option of manually testing the most recent sample or the reservoir could be removed and placed in the glucose analyzer supplied to the home, which would give the patient not only the current glucose level but also a history of the glucose levels since the last analysis, or alternatively the patient could take the sample collectors to the doctor for analysis by machine. In either the home or in the doctor's office, the information could be electronically recorded for transfer to the patient's record on a computer. The subject invention will provide much greater information about patient chemical changes than previously available by either venipuncture or finger stick. This increased information will allow better treatment and control of many clinical conditions.

What is claimed is:

1. A method for continuous long term monitoring of the blood level of a physiological constituent of blood, comprising the steps of:
    implanting a porous membrane filter within an interstitial body space in fluid communication with blood capillaries;
    filtering an ultrafiltrate of blood from the capillaries by exerting a negative pressure withdrawal force on the porous membrane filter so as to cause the ultrafiltrate to flow from the capillaries through the filter at a desired flow rate;
    collecting the ultrafiltrate in a reservoir located externally of the body; and
    assaying the ultrafiltrate to measure a desired physiological constituent thereof.

2. The method of claim 1 wherein said assaying step includes measuring the level of glucose in the ultrafiltrate.

3. The method of claim 1 wherein said filtering and collecting steps include filtering the ultrafiltrate along with a gas and collecting the ultrafiltrate inside said reservoir in distinct liquid boluses separated by the gas.

4. The method of claim 3 wherein said collecting step includes collecting the ultrafiltrate inside said reservoir in distinct liquid boluses separated by the gas in a volume ratio of gas to ultrafiltrate of about ten to one.

5. The method of claim 1 wherein said filtering step is accomplished at a flow rate in a range from about 20 to 500 microliters per hour.

* * * * *

UNITED STATES PATENT AND TRADEMARK OFFICE
CERTIFICATE OF CORRECTION

PATENT NO. : 4,777,953

DATED : October 18, 1988

INVENTOR(S) : Stephen R. Ash and Elsa M. Janie-Swain

It is certified that error appears in the above-identified patent and that said Letters Patent is hereby corrected as shown below:

In Column 1, please insert the following after the title of the invention and before the BACKGROUND OF THE INVENTION --This invention was made with government support under grant number B43 DK 35550-01A1S awarded by the National Institutes of Health. The government has certain rights in the invention.--

Signed and Sealed this

Twenty-second Day of June, 1993

Attest:

MICHAEL K. KIRK

Attesting Officer     Acting Commissioner of Patents and Trademarks